| United States Patent [19] | [11] | 4,264,610 |
|---|---|---|
| Clifford | [45] | Apr. 28, 1981 |

[54] N,N'-BIS(2,6-BIS(TRIFLUOROMETHYL)-4-PYRIDINYL)ETHANEDIAMIDE AND ITS USE AS A COCCIDIOSTAT

[75] Inventor: David P. Clifford, King's Lynn, England

[73] Assignee: Dow Chemical Company Limited, King's Lynn, England

[21] Appl. No.: 160,404

[22] Filed: Jun. 17, 1980

[51] Int. Cl.³ .................. A61K 31/435; C07D 213/75
[52] U.S. Cl. .................................... 424/263; 546/265
[58] Field of Search ........................ 546/265; 424/263

[56] References Cited

U.S. PATENT DOCUMENTS 3,906,033  9/1975  Biland et al. ..................... 260/479 R Primary Examiner—Henry R. Jiles
Assistant Examiner—Natalia Harkaway
Attorney, Agent, or Firm—S. Preston Jones; Ronald G. Brookens

[57] ABSTRACT

N,N'-Bis(2,6-Bis(trifluoromethyl)-4-pyridinyl)ethanediamide and its use in controlling coccidia is taught.

3 Claims, No Drawings

N,N'-BIS(2,6-BIS(TRIFLUOROMETHYL)-4-PYRIDINYL)ETHANEDIAMIDE AND ITS USE AS A COCCIDIOSTAT

SUMMARY OF THE INVENTION

This invention relates to animal husbandry and more particularly to methods and compositions adapted to be employed for improving the growth of animals, for improving the efficiency of the utilization of animal feed, for controlling protozan organisms and for mitigating against the attack of gastro-intestinal parasites.

The present invention provides an improved method for raising and benefiting animals including fowl. The invention particularly provides a new and improved method for mitigating against and protecting animals from the attack of gastro-intestinal parasites and protozoan organisms, particularly coccidia. In addition, the invention provides a method of improving the nutritive value of the feed ingested and utilized by animals so as to obtain a growth-furthering effect and an improved feed utilization.

The invention also provides novel compositions adapted to be employed in the new methods in animal husbandry.

The present method comprises administering to animals an effective amount of N,N'-bis(2,6-bis(trifluoromethyl)-4-pyridinyl)ethanediamide.

By the practice of the present invention nutritive value of animal feed can be improved so as to obtain a growth-furthering effect and improves the efficiency of the utilization of feed by animals. The practice also makes possible improvement of the growth made by the animals and protection of the animals from parasitic diseases of the gastro-intestinal tract and particularly from coccidiosis. Further, by the practice of the invention animals can be protected from mixed coccidial infections and from the various strains of the same species of coccidial organism and particularly from the various strains of *Eimeria tenella* and *acervulina*. Also, the practice allows animals which are exposed to the coccidial infection to develop acquired immunity to the disease.

The compound of the present invention is a crystalline solid, m.p. 271°–272.5° C., which is somewhat soluble in organic solvents and is adapted to be administered to animals. The compound can be employed in admixture with grain rations of animals feeds. It can be administered continuously or intermittently in dosages sufficient to improve growth, to improve the feed efficiency, to improve the nutritive value and utilization of feed, or to protect the animal from the attack of gastro-intestinal parasites without adversely affecting the metabolic activity, reproduction or the blood-forming organs, or without imparting any unpalatable characteristic to animal flesh.

In the oral administration or feeding of the compound, good results can be obtained when the animals are fed a daily dosage of from about 3 to about 2,000 milligrams of the compounds per kilogram of body weight and preferably from about 3 to about 250 milligrams per kilogram of body weight. Where danger of re-exposure to the attack of intestinal parasites from contaminated feed or surroundings is low, good results can be obtained when the animals are fed a daily dosage of about 35 milligrams or more per kilogram of body weight for a period of from 2 to 5 days.

The method of the present invention can be carried out by the oral administration or feeding of the unmodified compound. However, the present invention also embraces the employment of a liquid, powder, mash, pellet, capsule or animal food containing said compound. In such usage, the compound can be modified with one or more of a plurality of additaments or innocuous ingestible adjuvants including water, ethanol, skim milk, edible oils, propylene glycol, syrups, grain rations, surface active dispersing agents such as the liquid and solid emulsifying agents and edible solid carriers such as edible powders and commercial animal feeds, concentrates or supplements. The expression "commercial animal feeds, concentrates or supplements" as used herein includes the partial and complete animal feeds containing desirable amounts of minerals, vitamins, antioxidants, antibiotics and growth stimulants. In such animal feed compositions, the adjuvant can cooperate with the active agent so as to facilitate the invention and obtain an improved result. Further, the compositions can be adapted to be fed to animals to supply the desired dosage of active agent, or to be employed as concentrates and subsequently diluted with additional carrier or adjuvant to provide the ultimate compositions.

The exact concentration of the compound to be employed in the compositions can vary depending on the method of administration. For example, where direct administration to the individual animal is preferred, liquid or solid compositions containing from 5 to 98 percent by weight of the agent conveniently can be employed to supply the desired dosage. Where the compound is provided as a constituent of the principal food ration, satisfactory results can be obtained with food rations containing a minor but effective amount of the compound. The exact amounts of the compound in the ration are dependent upon the food consumption and feeding habits of the animal concerned. In fowl, the required dosages can be supplied with mash compositions containing from about 0.001 to about 0.1 percent by weight of the active agent. In animals such as pigs, the required dosage can be supplied with mash compositions containing from about 0.001 to about 0.5 percent by weight of active material when fed as the principal food ration. Where the compound is furnished in the drinking water, good results can be obtained at concentrations of the agent in the water equal to one-half those employed when the compound is supplied as a constituent in the principal food ration. In compositions to be employed as concentrates, the active agent can be present in a concentration of from about 5 to about 98 percent by weight. Preferred concentrate compositions oftentimes contain two or more percent by weight of a liquid or solid surface active agent.

Liquid compositions containing the desired amount of the compound can be prepared by dissolving the compounds in ethanol, propylene glycol or an edible oil or by dispersing in water with or without the aid of a suitable surface active dispersing agent such as an ionic or non-ionic surface active agent. Suitable surface active dispersing agents include the glycerol and sorbitan esters of fatty acids and the polyoxyalkylene derivatives of fatty alcohols and of sorbitan esters. The aqueous compositions can contain one or more water-immiscible oils as a solvent for the active agent. In such compositions, the water, oil and emulsifying agent constitute an aqueous emulsion adjuvant or helper.

In the preparation of solid feed compositions, the compound can be mechanically ground with an edible solid such as cereal meal, oyster shell flour, or a solid surface active dispersing agent such as finely divided bentonite or fuller's earth. These compositions can be administered in the form of capsules or tablets or dispersed in an animal feed and such feed used to supply a part or all of the ration. Alternatively, the compound can be dissolved in an organic solvent such as alcohol or acetone and the resulting mixture dispersed in an animal feed which is then dried to remove the solvent. The compound can also be dispersed in an edible oil such as coconut, olive, cottonseed or peanut oil and the resulting mixtures dispersed in the feed. These edible oil compositions can contain one of the aforementioned emulsifying materials as a dispersing agent.

The following examples illustrate the invention.

EXAMPLE 1

N,N'-Bis(2,6-bis(trifluoromethyl)-4-pyridinyl)ethanediamide

To a stirred and refluxing solution of oxalyl chloride (64 grams (g), 43 mls 0.5 mole) in dry benzene (100 mls) was added a slurry of 4-amino-2,6-(bis-trifluoromethyl)-pyridine (20 g 0.037 mole) in warm benzene (150 mls) over a period of 60 minutes. The mixture was then heated under reflux for 5 hours and filtered hot. The titled product was recovered as a cream colored solid in a yield of 57 grams melting at 271°–272.5° C.

The product after recrystallization from benzene containing about 1–2% ethanol was recovered as colorless needles melting at 271°–272.5° C.

Analysis: $C_{16}H_6F_{12}N_4O_2$. Required: C, 37.35; H, 1.17; N, 10.89. Found: C, 37.35; H, 1.33; N, 10.93.

EXAMPLE 2

N,N'-Bis(2,6-bis(trifluoromethyl)-4-pyridinyl)ethanediamide was dispersed in commercial poultry mash to produce feed compositions containing various amounts of the compound. Portions of these compositions and unmodified mash were fed as a sole feed ration to flocks of chickens of like history and past environment which were about 17 days old. One day after the diets were begun the chickens were orally administered 2,000,000 oocysts of *Eimeria acervuliva*. There were 5 chicks per replicate and 3 replicates per treatment for a total of 15 chicks. The tests were repeated with innoculated unmedicated chicks, (I.U.C.) and uninnoculated unmedicated chicks (U.U.C.), to serve as checks. The results were as follows:

| Treatment | Percent by Weight of Agent in Feed | % Weight Gain in Eleven Days |
| --- | --- | --- |
| 1 | 0.025 | 84.0 |
| 2 | 0.0125 | 74.5 |
| 6 I.U.C. | — | 63.0 |
| 7 U.U.C. | — | 102.0 |

There was no mortality in any of the tests.

EXAMPLE 3

The above procedures were repeated except that test chickens were orally given 400,000 oocysts of *Eimeria tenella* one day after the diets were begun. The results were as follows:

| Treatment | Percent by Weight of Agent in Feed | % Weight Gain in 11 Days | Mortality |
| --- | --- | --- | --- |
| 1 | 0.0250 | 76.0 | 0/15 |
| 2 | 0.0125 | 14.5 | 5/15 |
| 3 I.U.C. | — | Zero | 8/15 |
| 4 U.U.C. | — | 102.5 | 0/15 |

In further embodiments, the compound as employed in accordance with the present invention, or compositions containing the same, advantageously can be employed in the present methods in combination with one or more other feed additives including agents active against gastro-intestinal parasites, either as adjuvants or supplemental materials. Representative additives and agents include 2-sulfanilamidoquinoxaline, acetyl(p-nitrophenyl) sulfanilamide, sulfadimethylpyridine, 2,2'-methylene bis(4-chlorophenol), 4,4'-isopropylidene bis-(o-cresol), 5-nitro-2-furaldehyde semicarbazone, furoxone N-(5-nitro-2-furfurylidene-3-amino-2-oxazolidone), 3-nitro-4-hydroxyphenyl arsonic acid, p-aminobenzene arsonic acid, the complex of 4,4'-dinitrocarbanilide and 2-hydroxy-4,6-dimethylpyrimidine, 4,5-imidazole dicarboxamide, methyl-4-acetamido-2-ethoxybenzoate, oxytetracycline, chlorotetracycline, N-(4'-chlorophenyl)-7-oxabicyclo(2.2.1)heptane-2,3-dicarboximide, methyl-4-acetamido-2-ethoxybenzoate, tetraethyl thiuram disulfide, arsenosobenzene, 5-nitro-2-furaldehyde acetohydrazone, 2,2'-dihydroxy-3,3',5,5'-tetrachlorodiphenylsulfide, 4,6-diamino-2,2-dimethyl-1,3,5-triazine hydrochloride, sulfamethazine, sulfamerazine, sulfadimidine, 2,4-diamino-5-(p-chlorophenyl)-6-ethylpyrimidines, 2,4-diamino-5-(3,4-dichlorophenyl)-6,6-diethyl-5,6-dihydro-1,3,5-triazines, 3,5-dinitrobenzamide, 3,5-dinitro-o-toluamide, 2-chloro-4-nitrobenzamide and other anologues 2,4-diamino-5-aryl-6-alkylpyrimidines, 2,4-diamino-5-aryl-6,6-dialkyl-5,6-dihydro-1,3,5-triazines, dinitrobenzamides, 3,5-dichloro-2,6-dimethylpyridinol, monensin and dinitrotoluamides.

In representative operations, each of the feed additives identified in the preceding paragraph together with the compound of this invention are mechanically mixed and ground with commercial poultry mash to produce animal feed compositions. In such operations, the materials are advantageously employed in amounts sufficient to provide feed compositions containing about 0.0125 percent by weight of one of the feed additives identified in the preceding paragraph and about 0.008 percent by weight of one compound of this invention.

These compositions are of excellent value in animal husbandry and are adapted to be fed to fowl to obtain a growth-furthering effect and superior feed efficiency and to mitigate against the attack of protozoan organisms and particularly Eimeria organisms.

What is claimed is:

1. N,N'-bis(2,6-bis(trifluoromethyl)-4-pyridinyl)ethanediamide.

2. Poultry feed containing a coccidiostatically effective amount of N,N'-bis(2,6-bis(trifluoromethyl)-4-pyridinyl)-ethanediamide.

3. A method for improving the growth of poultry comprising administering to the poultry a feed composition containing from about 0.001 to about 0.1 percent by weight of N,N'-bis(2,6-bis-(trifluoromethyl)-4-pyridinyl-ethanediamide.

* * * * *

UNITED STATES PATENT AND TRADEMARK OFFICE
CERTIFICATE OF CORRECTION

PATENT NO. : 4,264,610

DATED : April 28, 1981

INVENTOR(S) : David P. Clifford

It is certified that error appears in the above—identified patent and that said Letters Patent is hereby corrected as shown below:

Column 1, line 49, reading "of" should read -- or --.

Column 1, line 49, reading "animals" should read -- animal --.

Column 3, line 37, reading "pyridiny" should read -- pyridinyl --.

Signed and Sealed this

Thirteenth Day of October 1981

[SEAL]

Attest:

GERALD J. MOSSINGHOFF

Attesting Officer

Commissioner of Patents and Trademarks